United States Patent [19]

DeKont

[11] 4,087,637
[45] May 2, 1978

[54] PACER PULSE WIDTH SIGNALING SYSTEM FOR TELEPHONIC COMMUNICATION

[75] Inventor: Ervin Christopher DeKont, Plantation, Fla.

[73] Assignee: ESB Incorporated, Philadelphia, Pa.

[21] Appl. No.: 721,299

[22] Filed: Sep. 8, 1976

[51] Int. Cl.² .................. H04M 11/00; A61B 5/02
[52] U.S. Cl. ............................ 179/2 A; 128/2.1 A
[58] Field of Search .............. 179/2 R, 2 A, 2 DP; 128/2.1 A, 2.06 R, 2.06 E, DIG. 4; 307/265, 267, 268

[56] References Cited

U.S. PATENT DOCUMENTS

| 3,426,150 | 2/1969 | Tygart | 179/2 DP |
|---|---|---|---|
| 3,742,938 | 7/1973 | Stern | 128/2.1 A |
| 3,986,496 | 10/1976 | Brastad | 128/2.1 A |

Primary Examiner—Kathleen H. Claffy
Assistant Examiner—Joseph A. Popek
Attorney, Agent, or Firm—Gary V. Pack; Anthony J. Rossi; Gilbert W. Rudman

[57] ABSTRACT

A system for providing a signal suitable for transmission by telephone equipment to indicate the duration of pulses produced by a heart pacer. The system includes a pickup for detecting pacer pulses and a switched circuit responsive to pulse duration for applying charge to a first capacitor. During the inter-pulse period a second or reference capacitor is charged to a level corresponding to that of the first capacitor though a timed switching circuit, after which another timed switching circuit discharges the first capacitor to prepare it for receiving a subsequent charge. The potential accumulated upon the second capacitor is then used to operate an output stage pulse generator which controls the duration of an audio-frequency tone burst.

12 Claims, 2 Drawing Figures

PACER PULSE WIDTH SIGNALING SYSTEM FOR TELEPHONIC COMMUNICATION

BACKGROUND OF THE INVENTION

The present invention relates to an improvement in organ pacer sensing systems and, more specifically, to a system which allows short-duration pulses to be monitored over a communication line having only a low frequency transmission capability.

Various types of electrical organ stimulators have been developed and adapted to provide the stimuli needed to cause a defective or damaged organ to function properly. The most widely used of this type of apparatus is the battery powered electronic cardiac stimulator or "heart pacer" which is conventionally implanted beneath the skin of a user. Such implanted pacers are ordinarily self-contained and powered by a battery within the pacer casing. The pacer utilizes energy from a battery to generate electrical pulses which are applied via conductive leads to predetermined portions of an organ, such as a heart. The pulses generated by the pacer comprise artificial stimulation signals which supplant the periodic electrical stimulation signals which are naturally generated within the body for stimulating the organ. In general, a heart is electrically stimulated to beat once for each pulse which is generated by the pacer.

A number of different types of heart pacers have been developed and, while they are alike in that they supply electrical stimulation in a predetermined fashion, the timing and nature of the pulses may vary from one pacer to another. More important to the present description, the response of pacer operation to a decline in battery voltage, caused by faulty or aging battery, may differ substantially from one type of pacer to another.

The types of batteries which are best suited for energizing pacers conventionally exhibit a constant output voltage throughout most of their operative lives, then near the end of their lives the voltage declines in a relatively short period. With most types of pacer circuits, the pulse rate of the pacer decreases toward the end of battery life. Further, in one type of pacer the width of the output pulses increases as a result of decrease in battery voltage. With most types of pacers, however, the width or duration of the outputted pulses decreases as a function of battery voltage. Accordingly, the width of a pacer pulse is a valuable indication of battery voltage, and may also be used as a confirmation of the status of the battery.

In some modes of improper activity or failure of pacer circuitry the pulse rate may change, despite the fact that the status of the battery remains the same. At the same time, however, the width of the pulse will normally remain constant. Accordingly, a measure of the pulse width can serve to distinguish between a change in pulse rate due to circuit failure, and one due to a decline in battery charge.

Some newer types of pacers maintain a substantially constant pulse rate despite a decline in battery voltage; however, the change in pulse width is substantial and accordingly pulse width monitoring is the only feasible way of monitoring battery status. In such a pacer, the system is adapted to output a substantially constant burst of energy with each pulse so that as amplitude declines with battery aging, pulse width is caused to increase.

Apparatus are now known for detecting and transducing pacer signals, and coupling them to telephonic communication links so that they may be received and analyzed by equipment at a remote location. See for instance the abstract entitled "Transtelephone Pacemaker Clinic" by S. Furman, B. Parker and D. Escher, at page 94 of the *American Journal of Cardiology*, Vol. 25. Such systems are further described in U.S. Pat. Nos. 3,872,252 — Malchman et al. and 3,826,246 — Raddi et al. With such systems a pacer wearer can allow the battery in his implanted pacer to be checked regularly by a cardiologist or clinician at a distant location without the need for actual visits to the physician or clinician.

In the systems of interest pacer output pulses and/or cardiac signals are sensed by appropriate transducers and converted to acoustical signals which are transmittable by a telephone communication link. As is well known, commercial telephone links are responsive over only a narrow frequency band, extending from approximately 300 to 3000 Hz. While this relatively narrow band is adequate for the transmission of voice grade signals, it places severe constraints upon the transmission of more complex information. In the instance of interest, the pacer pulses which are desired to be monitored exhibit a duration or width of from approximately one-half to two milliseconds, and accordingly cannot be resolved over telephonic links with sufficient accuracy to allow changes in pulse duration to be detected.

Accordingly, it will be seen that it would be highly desirable to provide a system for producing telephonically transmittable signals which accurately represent the pulse width of electric pacer pulses.

It is accordingly an object of the present invention to provide means for converting a detected pacer pulse into an acoustically transmissible signal.

Another object of the invention is to provide a circuit responsive to a high frequency pacer pulse to produce a lower-frequency representation thereof.

Still another object is to provide an improved monitoring means for producing a representation of the duration of detected pacer pulses which can be transmitted over conventional telephone equipment.

SUMMARY OF THE INVENTION

Briefly stated, in accordance with one aspect of the invention the foregoing objects are achieved by providing means for switchably charging a first capacitor in response to a detected pacer pulse, and means for thereafter charging a second capacitor to a voltage level representative of the charge accumulated upon the first capacitor. Subsequent to the charging of the second capacitor, the first capacitor is discharged so as to be made ready to accept a subsequent quantum of charge pursuant to another pacer pulse. The voltage level of the second capacitor is then used to operate a voltage controlled pulse generator to cause a train of telephonically transmittable signals to be outputted which display a characteristic representative of the voltage upon the second capacitor.

In a preferred embodiment a pulse splitter is used to produce a pair of trigger pulses in response to a single pacer pulse, for sequentially energizing and deenergizing the first capacitor charging circuit. The signal outputted by the system comprises an interrupted tone burst in the range of 300 to 3000 Hz, the period of the burst representing the width of the detected pacer pulse.

BRIEF DESCRIPTION OF THE DRAWINGS

While the specification concludes with claims particularly pointing out and distinctly claiming the subject matter which is regarded as the invention, it is believed that the invention will be better understood from the following description of a preferred embodiment taken in conjunction with the accompanying drawings in which:

DESCRIPTION OF A PREFERRED EMBODIMENT

Figure 1:
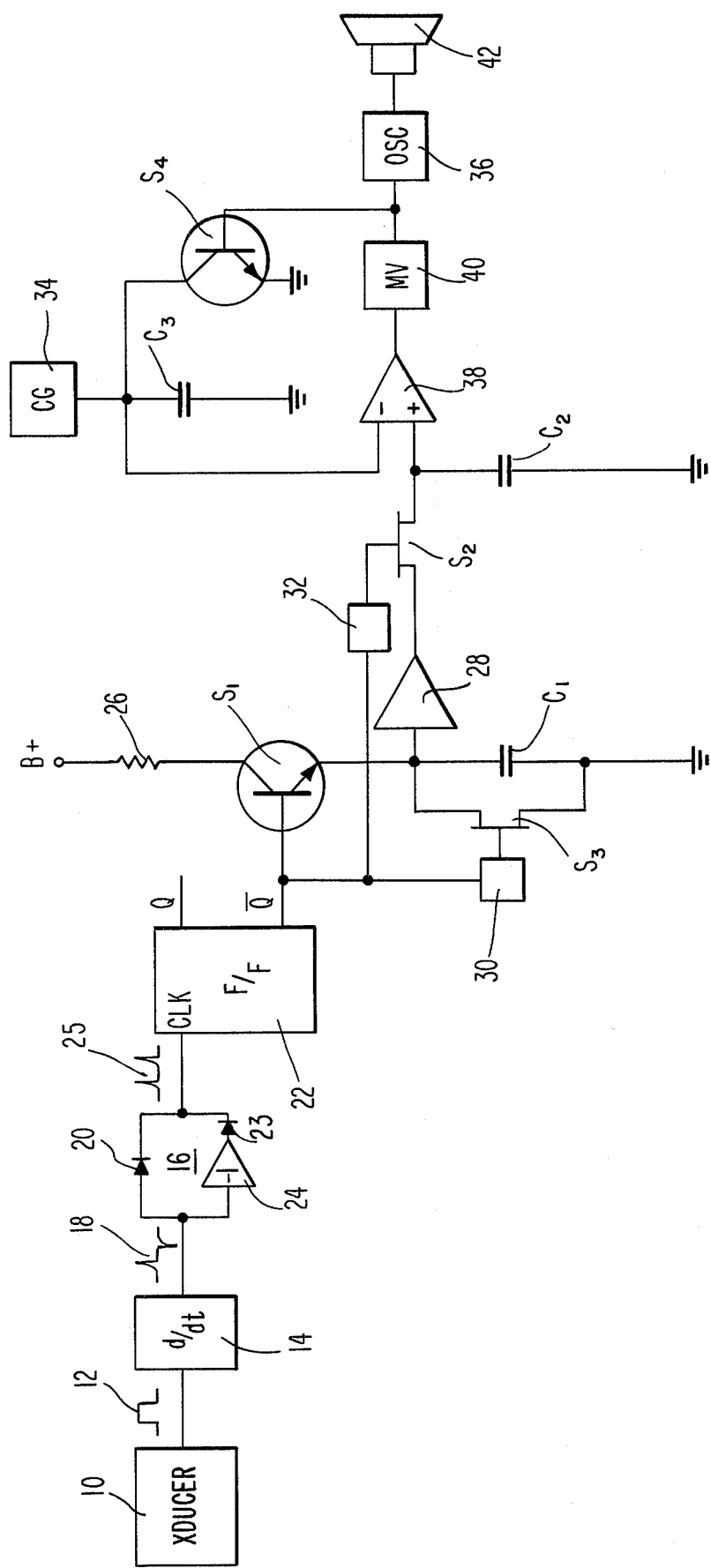
FIG. 1 is a schematic representation of a preferred embodiment.

In order to detect the signals outputted by a pacer unit, a transducer 10 of an appropriate type is placed in close proximity to the pacer. While the specific type of transducer comprises no part of the present invention, it may advantageously be of the type described in U.S. Pat. Nos. 3,872,252 and 3,826,246 referred to above. Alternatively, any appropriate transducer sensitive to the type of impulses produced by a given pacer may be selected for use. The transducer outputs a signal 12 which is advantageously a square wave having a duration or width identical to that of the pacer pulse. Preferably, pulse 12 comprises a virtual replica of the detected pacer pulse.

The signal outputted by transducer 10 is then passed to a pulse splitter which includes a differentiator 14 and a rectifier stage 16. The differentiated signal which is produced in response to the square wave 12 comprises a pair of oppositely-directed spikes 18, the positive-going one of which is coupled through diode 20 of the rectifier stage 16 to a current gate stage comprising a bistable element such as flip-flop 22. The negative-going spike is passed through inverter 24 and diode 23 of the rectifier stage to the flip-flop so that the CLK input of the flip-flop receives a pair of sharply-defined, positive-going trigger pulses 25 which are displaced in time by an amount equivalent to the duration of the pacer pulse. The transducer, differentiator and rectifier may thus be considered to comprise a pickup stage for processing signals which activate the bistable flip-flop.

Coupled to one of the toggle outputs Q and $\bar{Q}$ of flip-flop 22 is a switch S1 which, in a preferred embodiment, comprises a transistor. Transistor S1 serves to couple a first capacitor C1 to a source of potential B+ through a resistor 26 and in this manner provides a source of substantially constant current for charging capacitor C1. Capacitor C1 is in turn connected to an input terminal of an amplifier 28, which may be an operational amplifier having a gain of unity, and then through a switch S2 to a second capacitor C2. While switch S2 may be of any appropriate type, in one successfully tested embodiment a field effect transistor was used.

A third switching element S3 is coupled in circuit about a capacitor C1 and is responsive to a first timing circuit 30 for discharging C1 at intervals as determined by the operation of flip-flop 22. A second, similar timing circuit 32 is operative to activate switching means S2 at appropriate times to allow capacitor C2 to attain a potential representative of the voltage accumulated upon capacitor C1. In this manner the voltage existing upon capacitor C2 at any given time is representative of the duration of the last-detected pacer pulse.

In order to produce a telephonically transmittable signal representative of the voltage of capacitor C2, a voltage controlled pulse generator stage is provided. The latter includes a current generator 34 of an appropriate type, which is coupled to a third capacitor C3. The voltage upon capacitor C3 determines the timing of a signal to be applied to an oscillator 36. The oscillator is adapted to produce an audible tone lying in a frequency range within the capabilities of the telephonic communication link to be used.

A comparator 38 is coupled to both capacitors C2 and C3 as shown, and the output of the comparator applied through a one-shot multivibrator 40 to oscillator 36 and to a switch S4, which may be a transistor. The multivibrator drives the transistor into conduction at appropriate times in order to discharge capacitor C3 and to disable oscillator 36. A speaker or the like 42 is provided for actually producing an audible signal for pickup by the telephonic communication link (not shown) which conventionally comprises an ordinary telephone receiver handset.

Figure 2:
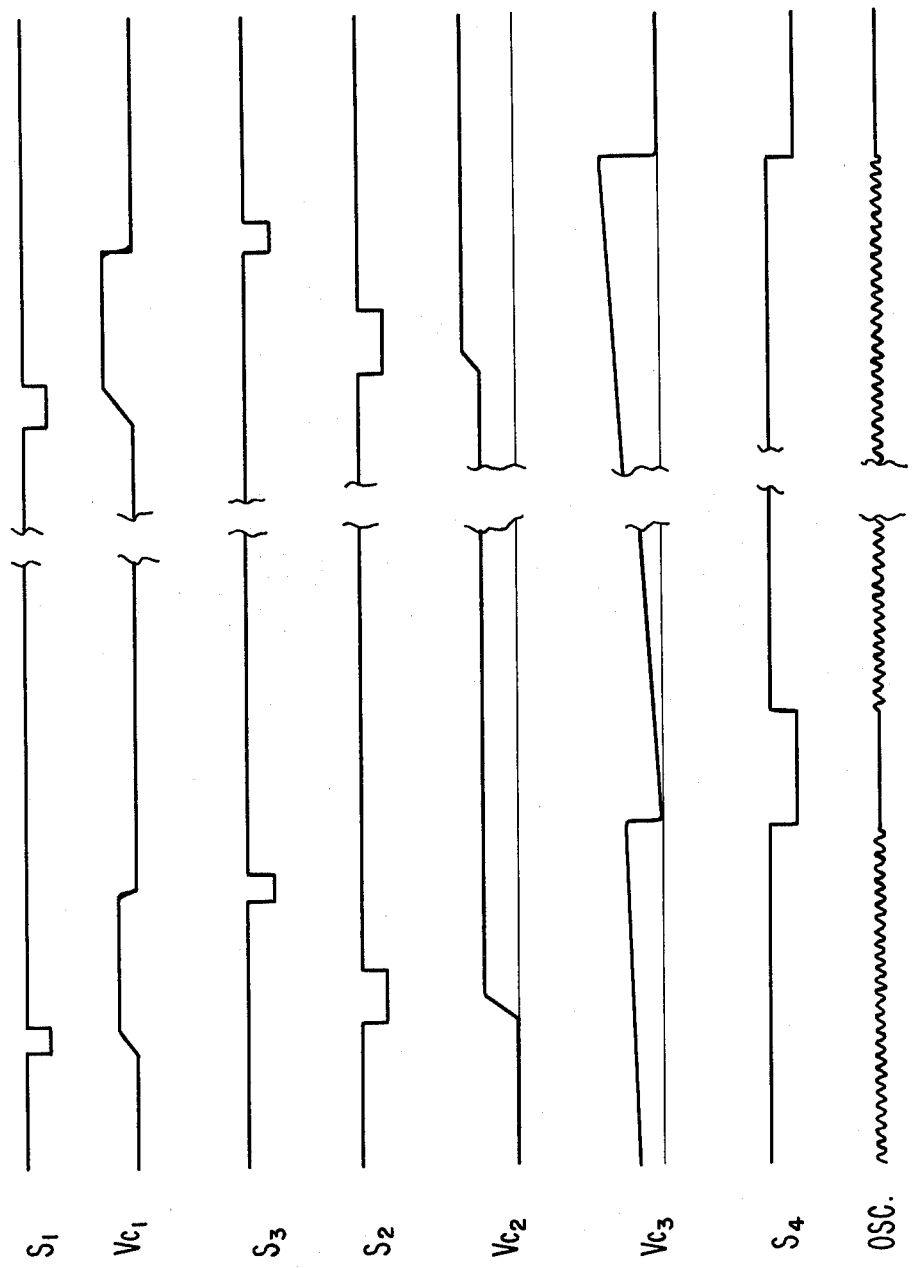
FIG. 2 is a timing diagram illustrating the operation of the system of FIG. 1.

The operation of the system of FIG. 1 will now be discussed in detail, making reference to the waveshapes of FIG. 2. It is to be understood that FIG. 2 is included for illustrative purposes to provide an idealized representation of waveforms at various parts of the circuit, rather than a precise reproduction of waveforms actually encountered in use. The various waveforms are intended to correspond to the voltages arising across the circuit elements which bear corresponding designations.

As transducer 10 is placed in operative proximity to a pacer, a generally square wave signal 12 is produced. The signal is differentiated as shown by splitter 14 and a pair of trigger pulses 25, which comprise a rectified, differentiated replica of signal 12, are applied to flip-flop 22. The signals which have thus been processed by the pickup stage of the system are used to trigger the flip-flop, causing it to change state twice for each pacer pulse.

The signal appearing upon one of the two complementary flip-flop outputs Q and $\bar{Q}$ is coupled to the base terminal of switching transistor S1. In the depicted embodiment, the first-received trigger pulse causes the $\bar{Q}$ terminal of flip-flop 22 to assume a "high" status and accordingly bias switch transistor S1 into a conductive mode. The current then flows to the capacitor C1 so as to effect a substantially linear increase in voltage upon the capacitor, as evidenced by waveform VC1. After a period of time equivalent to the width of pulse 12 has elapsed, the second trigger signal causes flip-flop 22 to change state once more, dropping the $\bar{Q}$ output and causing switching transistor S1 to assume a non-conductive or blocking mode. At this point the voltage across capacitor C1 stabilizes. Subsequent to this the timing stage 32, which may for example comprise a simple RC timing circuit, causes switching transistor S2 to become conductive, coupling capacitor C1 to capacitor C2 by way of amplifier 28. The amplifier causes the voltage upon capacitor C2 to rapidly increase to the level of capacitor C1 and thereafter delay circuit 32 causes switching transistor S2 to become disabled, thus isolating capacitor C2 from the preceding circuitry. The voltage upon capacitor C2 then stops increasing and remains constant.

A second time delay circuit 30, which may be of the same type as circuit 32, provides an appropriate delay to cause switching transistor S3 to become energized after adequate time has expired for switch S2 to complete its function. Thereafter, switching transistor S3 is enabled to short-circuit capacitor C1, rapidly discharging the latter and preparing it for the receipt of a subsequent quantum of charge which represents the width of a succeeding, detected pulse.

The foregoing procedure is repeated each time a pulse is detected by transducer 10 and applied by the pickup stage to flip-flop 22. Capacitor C2 is not purposely discharged during operation of the system, its level being adjusted each time capacitor C1 is charged so that the voltage upon capacitor C2 is incrementally modified to reflect the value of the previous charge by capacitor C1, and therefore the duration of the last-detected pacer pulse.

To provide a system for converting the voltage upon capacitor C2 to a telephonically transmittable acoustic signal, a third capacitor C3 is provided and coupled to a current generator 34. Although in the preferred embodiment a current generator is utilized so as to achieve a linear rate of voltage rise across the capacitor it will readily be appreciated that non-linearities may be introduced here, as in other parts of the system, and subsequently compensated for either in the present system or by corresponding non-linearities in a receiving device. Accordingly, the term "current generator" is used in the broad sense to denote an appropriate source of charging current for capacitor C3.

Comparator 38 is coupled to both capacitors C2 and C3 and is adapted to produce a signal when the voltage monitored by its "invert" terminal, i.e. the voltage upon capacitor C3, exceeds the voltage existing upon capacitor C2. At this instant, the amplifier signal energizes a single shot multivibrator 40 which produces a single pulse of fixed amplitude and duration for momentarily driving switching transistor S4 into conduction and for disabling oscillator 36 for a brief period.

At the initiation of a cycle capacitor C3 is discharged by the momentary conduction of switch S4, after which the capacitor voltage increases at a fixed rate as shown by curve VC3 in accordance with the characteristics of current generator 34. Gated oscillator 36 is disabled while the multivibrator produces an output pulse, and accordingly the tone produced by speaker 42 ceases briefly. At the end of the multivibrator pulse the tone resumes and continues until such time as the voltage across capacitor C3 equals that upon capacitor C2. At this juncture the multivibrator is again triggered and switching transistor S4 discharges capacitor C3. The time required for capacitor C3 to attain the same voltage as is on capacitor C2 is then an indication of the voltage last impressed upon capacitor C1 and thus a representation of pulse width. At the end of each charging period, the pulse produced by multivibrator 40 serves both to discharge capacitor C3 and to disable oscillator 36 for a fixed period. In this manner the duration of the oscillator output signal, or more precisely the period from the cessation of one signal to the cessation of the next, provides a telephonically transmittable analog of pacer pulse width.

Upon the detection of a succeeding pacer pulse, capacitor C1 is again charged to a voltage which reflects the duration of the pulse. In the instance wherein the second, succeeding pulse is longer than its predecessor, as illustrated in FIG. 2, transistor S1 is enabled for a correspondingly longer period. Voltage VC1 then attains a higher value and accordingly when switching means S2 is enabled the voltage VC2 upon capacitor C2 is increased by an amount proportional to the increase in pacer pulse width.

The voltage VC3 upon capacitor C3 must now attain a correspondingly higher value before comparator 38 effects its discharge via multivibrator 40 and switch S4. This in turn extends the period of time between the achievement of the minimum oscillator-enabling voltage Vo and the discharge of capacitor C3. As a consequence, the duration of the oscillator burst is increased to indicate the width of the last-detected pacer pulse.

Once having understood the foregoing description it will occur to those skilled in the art that other modifications and applications of the illustrated system are possible. It may, for instance, be feasible in a given application to provide an audio-frequency oscillator whose frequency is a function of the voltage accumulated upon a capacitor, representing the duration of a detected pacer pulse. Alternatively, individual pulses may be outputted to define a time period whose length comprises an analog of pacer pulse width. These and other modifications and applications are considered to be within the scope of the present invention, and it is accordingly intended that dependent claims shall cover all such modifications and applications as do not depart from the true spirit and scope of the invention.

What is claimed as new and desired to be secured by Letters Patent of the United States is:

1. In a system for monitoring the operation of an implanted organ pacer via a telephonic communication link, means for producing an acoustically transmittable signal representing the width of pacer pulses, comprising:
    a pickup stage for detecting a pacer pulse and outputting an electrical pulse signal in response thereto;
    a current source;
    a first capacitor;
    first switching means coupled to said current source and said first capacitor and responsive to signals from said pickup stage for controlling the accumulation of charge on said first capacitor;
    a second capacitor;
    second switching means for coupling said first and said second capacitors;
    means for operating said second switching means subsequent to the operation of said first switching means to allow said second capacitor to charge to a potential representative of the potential on said first capacitor, and to thereafter electrically isolate said second capacitor from said first capacitor;
    third switching means coupled to said first capacitor;
    means for operating said third switching means subsequent to the operation of said second switching means to substantially discharge said first capacitor; and
    voltage controlled pulse generator means coupled to said second capacitor and responsive to voltage accumulated upon said second capacitor to output a train of pulses representative of the voltage accumulated upon said second capacitor.

2. A system according to claim 1, further including buffer amplifier means coupled between said first and said second capacitor.

3. A system according to claim 2, wherein said switching means comprise solid-state electronic switches.

4. A system according to claim 3, wherein said means for operating said second and said third switching means comprise time delay circuits.

5. A system according to claim 4, wherein said time delay circuits are coupled to said pickup stage and are responsive to said electrical pulse signal for operating said second and said third switching means.

6. A system according to claim 3, wherein said voltage controlled pulse generator comprises a gated oscillator and a transducer coupled thereto for outputting bursts of audio-frequency signals whose periods represent the voltage accumulated upon said second capacitor.

7. A system according to claim 6, wherein said transducer comprises a speaker coupled to said gated oscillator for outputting an audible signal for transmission by a telephonic communication link.

8. A system for monitoring the operation of an organ pacer via a telephonic communication link, comprising:
transducer means for detecting pacer pulses and outputting electrical pulses having a pulse width representative of the duration of the pacer pulses;
a pulse splitter coupled to said transducer means and responsive to said electrical pulses to produce two trigger pulses displaced in time by substantially the duration of one of said electrical pulses;
a bistable element coupled to said phase splitter and responsive to said trigger pulses for alternating state upon receipt of each pulse;
a first capacitor;
a gated current source coupled to said bistable element and to said first capacitor for charging said first capacitor when said bistable element is in a first state and for preventing said capacitor from charging when said bistable element is in a second state;
first switching means coupled to said first capacitor for discharging said capacitor;
a second capacitor;
second switching means coupled to said second capacitor for periodically causing said second capacitor to be charged to and held at a potential representative of the potential of said first capacitor;
a third capacitor;
current generator means for charging said third capacitor at a predetermined rate;
third switching means coupled to said second and said third capacitors for discharging said third capacitor when the potential on said third capacitor has attained a predetermined relationship with respect to the potential on the second capacitor; and
signal generating means coupled to said third switching means for producing a telephonically transmittable signal representing the period of each cycle of said third capacitor.

9. A system according to claim 8, wherein said pulse splitter comprises a differentiator for producing first and second pulses at the leading and trailing edges, respectively, of each of said electrical pulses; and
rectifying means coupling said differentiator to said bistable element for applying pulses having the same polarity to said bistable element.

10. A system according to claim 9, further including amplifier means coupled between said first and said second capacitor for causing said second capacitor to attain a potential proportional to the potential on said first capacitor.

11. A system according to claim 10, wherein said gated current generator comprises a source of charging potential and transistor means for switchably coupling said potential source with said first capacitor.

12. A system according to claim 11, wherein said third switching means comprises a comparator having a first input coupled to said second capacitor and a second input coupled to said third capacitor for outputting a signal when the potential on said third capacitor has attained a predetermined value with respect to the potential on said second capacitor;
means coupled to said comparator for outputting a switching pulse; and
switch means coupled to said last-named means and responsive to said switching pulse for discharging said third capacitor.

* * * * *